(12) United States Patent
Kilcoin et al.

(10) Patent No.: US 6,190,619 B1
(45) Date of Patent: Feb. 20, 2001

(54) SYSTEMS AND METHODS FOR PARALLEL SYNTHESIS OF COMPOUNDS

(75) Inventors: Christopher Kilcoin, Los Altos Hills; Steve Miller, Palo Alto, both of CA (US); Terry Long, Tucson, AZ (US)

(73) Assignee: Argonaut Technologies, Inc., San Carlos, CA (US)

( * ) Notice: Under 35 U.S.C. 154(b), the term of this patent shall be extended for 0 days.

(21) Appl. No.: 09/095,731

(22) Filed: Jun. 10, 1998

Related U.S. Application Data (60) Provisional application No. 60/049,198, filed on Jun. 11, 1997, and provisional application No. 60/063,134, filed on Oct. 22, 1997.

(51) Int. Cl.[7] .............................. B01L 11/00; B01L 3/00; B01J 10/00
(52) U.S. Cl. .................. 422/131; 422/102; 422/103; 422/916; 422/938; 422/937
(58) Field of Search .................. 422/130, 131, 422/132, 136, 58, 100, 102, 103, 63, 916, 937, 938; 215/309, 310, 313; 435/286.2, 286.4; 436/180, 43

(56) References Cited

U.S. PATENT DOCUMENTS

| | | | |
|---|---|---|---|
| 2,961,228 | * 11/1960 | Moore | 432/262 |
| 3,855,997 | * 12/1974 | Sauer | 600/573 |
| 4,538,653 | * 9/1985 | Shea et al. | 141/285 |
| 4,726,932 | * 2/1988 | Feier et al. | 422/103 |
| 4,746,491 | 5/1988 | Öhlin | 422/103 |
| 4,773,446 | * 9/1988 | Farnsworth et al. | 137/606 |
| 5,019,348 | 5/1991 | Ohms et al. | 422/63 |
| 5,424,038 | 6/1995 | Benz et al. | 422/100 |
| 5,503,805 | 4/1996 | Sugarman et al. | 422/131 |
| 5,565,171 | 10/1996 | Dovichi et al. | 422/68.1 |
| 5,605,666 | 2/1997 | Goodale et al. | 422/103 |
| 5,660,294 | * 8/1997 | Schneider et al. | 220/253 |
| 5,660,792 | 8/1997 | Koike | 422/63 |
| 5,762,881 | * 6/1998 | Harness et al. | 422/132 |
| 5,866,342 | * 2/1999 | Antonenko et al. | 435/7.1 |
| 5,888,830 | * 3/1999 | Mohan et al. | 436/174 |

\* cited by examiner

Primary Examiner—Shrive Beck
Assistant Examiner—Susan Ohorodnik
(74) Attorney, Agent, or Firm—Townsend and Townsend and Crew LLP (57) ABSTRACT

Systems and methods for synthesizing chemical compounds using a plurality reaction vessels. In particular, the present invention provides a synthesis apparatus capable of holding a plurality of reaction vessels for parallel synthesis of multiple discrete compounds or for combinatorial libraries of compounds. In one embodiment, a synthesis apparatus comprises a frame having a plurality of reaction vessel-holding openings and a plurality of valves for use in parallel synthesis of a plurality of compounds within reaction vessels.

9 Claims, 11 Drawing Sheets

SYSTEMS AND METHODS FOR PARALLEL SYNTHESIS OF COMPOUNDS

CROSS REFERENCE TO RELATED APPLICATIONS

The present application is related to and claims the benefit of U.S. Provisional Patent Application Serial No. 60/049,198 entitled "Systems and Methods for Parallel Synthesis of Compounds" filed on Jun. 11, 1997, and U.S. Provisional Patent Application Serial No. 60/063,134 entitled "Systems and Methods for Combinatorial Synthesis of Arrays of Reaction" filed on Oct. 22, 1997. The full disclosure of both applications are incorporated herein by reference for all purposes.

BACKGROUND OF THE INVENTION

The present invention generally relates to methods and apparatus for the parallel synthesis of large numbers of molecularly diverse compounds. The present invention is particularly useful in generating combinatorial libraries of chemical compounds by simultaneously employing solid phase synthesis in a plurality of reaction vessels.

A standard method for searching for new chemical compounds employs the screening of pre-existing compounds in assays which have been designated to test particular properties of the compound being screened. Similarly, in designing compounds having desired physiochemical properties for general chemical applications, numerous compounds must be individually prepared and tested.

To reduce the time and expense involved in preparing and screening a large number of compounds for biological activity or for desirable physiochemical properties, technology has been developed for providing libraries of compounds for the discovery of lead compounds. Current methods for generating large numbers of molecularly diverse compounds focus on the use of solid phase synthesis. The generation of combinatorial libraries of chemical compounds by employing solid phase synthesis is well known in the art. For example, Geysen, et al. (*Proc. Natl. Acad. Sci. USA*, 3998 (1984) describe the construction of multi-amino acid peptide libraries; Houghton, et al. (*Nature*, 354, 84 (1991) and PCT Patent Pub. No. WO 92/09300) describe the generation and use of synthetic peptide combinatorial libraries for basic research and drug discovery; Lam, et al. (*Nature*,354, 82 (1991) and PCT Patent Pub. No. WO 92/00091) describe a method of synthesis of linear peptides on a solid support such as polystyrene or polyacrylamide resin.

The growing importance of combinatorial chemistry as an integral component of the drug discovery process has spurred extensive technological and synthetic advances in the field (Thompson, L. A.; Ellman, J. A. (1996) *Chem. Rev.* 96, 555–600). Founded in peptide synthesis devised by Merrifield, solid phase chemistry has emerged as the prominent method for construction of small molecule combinatorial libraries (see e.g. Merrifield, R. B. (1963) *J. AM. Chem. Soc.* 85, 2149–2154; (a) Terrett, N. K.; Gardner, M.; Gordon, D. W.; Kobylecki, R. J.; Steele, J. (1995) Tetrahedron 51(30), 8135–8173. (b) Gordon, E. M.; Barrett, R. W.; Dower, W. J.; Fodor, S. P. A.; Gallop, M. A. (1994) *J. Med. Chem.* 37, 1385–1401.).

To aid in the generation of chemical compounds, such as present combinatorial chemical libraries, scientific instruments should be developed which automatically perform many or all of the steps required to generate such compounds. In the past, multiple solid phase reactions have been conducted by heating a substrate attached to resin beads with appropriate reagents and solvents in a test tube immersed in a hot oil bath with rotating magnetic stir bar. Draining was accomplished by pouring the contents of the test tube through a filter. Back and forth operation between reacting and draining operation was very tedious and potentially exposed the reaction mixture to air.

Certain chemical processes require that the chemical reagents be kept under an inert or anhydrous atmosphere to prevent reactive groups from reacting with molecular oxygen, water vapor, or other agents commonly found in air. Working with repeated solvent and reagent washes in a number of reaction vessels was time consuming and possibly compromised the inert atmosphere in the reaction vessels. Conventional septum type devices may loose seal integrity after repeated penetrations by needles during such synthesis. Accordingly, there is a need for systems and methods for rapid synthesis of chemical compounds.

SUMMARY OF THE INVENTION

The present invention is directed to systems and methods for synthesizing chemical compounds. In particular, the present invention provides a synthesis apparatus for use with a plurality of reaction vessels for parallel synthesis of multiple discrete compounds or for combinatorial libraries of compounds.

In one aspect of the present invention, the synthesis apparatus of the present invention includes a frame having a plurality of reaction vessel-holding openings and a plurality of valves, where the reaction vessel-holding openings and the valves are aligned with one another. Each valve is movable between an open position and a closed position. In the open position, fluid can be delivered through the valve, and in the closed position, fluid is prevented from passing through the valve. In a preferred embodiment, the valve includes a first valve portion having a first sealing surface and a second valve portion having a second sealing surface. The sealing surfaces are slidably movable relative to one another. Preferably, the second valve portion comprises separate cap vents movable between first and second positions corresponding to the open and closed positions of said valve. The first valve portion may define a first manifold passage and a second manifold passage. Each cap vent preferably has a bypass path that connects the first manifold passage to the second manifold passage when the cap vent is in the second position. Advantageously, the bypass path allows for flushing of the first and second manifold passages to remove any contaminants or reagents left from previous fluid washes. The reduces the likelihood of accidentally introducing residual reagents into the environment of the reaction vessel. The first valve portion is also preferably adapted to be slidably connectable with a fluid conduit. The first manifold passage, second manifold passages, and the bypass path typically define a U-shaped passage when the valve is in the second position.

Additionally, the present invention typically includes an actuator for simultaneously actuating a plurality of valves. The simultaneously opening and closing of the valves for several reaction vessels allows for the parallel distribution of fluids to the reaction vessels, which increases the speed of the entire procedure. Furthermore, the first valve portion preferably comprises of elastomeric material capable of maintaining a seal between the first and second sealing surfaces over a temperature range of about −400 to 150° C. Use of such elastomeric materials increases the temperature range over which the present invention can operate. The first valve portion may be a fluid manifold made from an elastomeric material and an inert material. The elastomeric material may be directly integrated with the fluid manifold or be a separate layer attached to the manifold. In one embodiment, the separate layer of elastomeric material may be covered with a layer of friction-resistant material to improve durability while retaining the compliant nature of the elastomeric material. Preferably, the valve is compressed between the lid and the reaction vessel when the apparatus is in operation. The apparatus may include a bias element to maintain a seal between the valve and the fluid manifold during apparatus operation. The seal typically isolates the reaction vessel interior from molecular oxygen, water vapor or other agents in the external, ambient atmosphere.

In another aspect of the invention, the reaction vessels each have a cap vent mountable to an open top of the reaction vessel. The cap vent preferably comprises an outer sealing surface and an inner surface facing the interior, where the cap vent defines first and second fluid passages extending between the outer and inner surfaces. In one embodiment, the cap vent defines a bypass path opening onto the outer surface at spaced-apart positions on the outer surface. The spaced-apart positions are separated by a bypass distance. The first and second fluid passageways may open on to the outer surface at first and second positions. The first and second positions are separated by a distance equal to the bypass distance. Typically, the bypass path comprises a groove on the outer surface of the cap vent. The cap vent is rotatable relative to a sealing surface of said synthesis apparatus. The cap vent preferably includes a radial extensor for rotating cap vent.

In one configuration, the bypass path is a groove on an upper surface between the openings in the fluid passages. This typically allows the entire fluid delivery system to be washed while the reactions are occurring in reaction vessels. In addition, the groove allows purging of the fluid delivery system after, for example, the cassette has been removed from the rest of the fluid delivery system. This allows the fluid delivery system to be purged of gases, vapors, oxygen or other contaminants, while the valve maintains a closed inert environment.

In another aspect of the present invention, a method for accessing the interior of a reaction vessel for use in combinatorial synthesis includes providing at least one reaction vessel aligned with a valve comprising first and second valve portions. A fluid conduit coupled to a fluid source is slidably engaged to a passage in the first valve portion. A second valve portion is moved to align a passage in the second valve portion with said passage of the first valve portion to provide access to the interior of the reaction vessel. With such alignment, fluid is flowed from the fluid conduit into said interior of the reaction vessel. A plurality of the valves may be simultaneously actuated such as by moving a rake coupled to valves.

In another aspect of the present invention, a method for flushing a fluid delivery pathway according to the present invention includes providing a synthesis apparatus having a valve comprising a first valve portion and a second valve portion. A first valve portion is moved to align a bypass path with first and second passages in the second valve portion. Fluid can then be flowed from the first passage through the bypass path to the second passage to flush those passages of any reagents or contaminants in those passages.

A further understanding of the nature and advantages of the present invention may be realized by reference to the remaining portions of the specification and the drawings.

DESCRIPTION OF THE PREFERRED EMBODIMENT

The present invention provides an apparatus by which any variety of single compounds or combinatorial libraries may be created. The present invention is particularly useful for the solid phase synthesis of organic compounds, including peptides. For convenience, the remaining disclosure will be directed specifically to the solid phase synthesis or organic compounds. However, it will be appreciated that the system and method can be applied equally well to liquid-liquid chemistry, or for the synthesis of organic compounds in the solution phase.

The present invention is useful for rapidly generating and systematically synthesizing large numbers of molecules that may vary in their chemical structure or composition. The invention is further useful for randomly generating a large number of candidate compounds, then later optimizing those compounds which exhibit the most desirable properties.

For the synthesis of compounds, appropriate starting materials may be attached to a support. Preferred support materials include solid polymeric materials, such as polyacrylamide, polydextran, polyethylene glycol., polystyrene, cellulose, sephadex, resins, combinations thereof, and the like. Alternate support materials include glass, acrylic, latex, and ceramics. Synthetic reactions may be conducted on the support-bound starting materials to obtain the desired compounds which may then be cleaved from the support.

As will be readily apparent to one skilled in the art, the present invention may be employed in essentially any synthetic reaction. Thus, the present invention is useful in almost all of the synthetic reactions which are known to one of skill in the art, including, for example, peptide synthesis, acylation, alkylation, condensation, cyclization, halogenation, heterogeneous catalysis, hydrolysis, metallation, nitration, nucleophilic displacement, organometallic reactions, oxidation, reduction, sulfonation, acid chloride formation, Diels-Alder reaction, Friedel-Crafts reactions, Fischer indole synthesis, Michael, reactions, and the like (see e.g., H.O. House, "Modern Synthetic Reactions", 2nd ed. (Benjamin/Cummings, Menlo Park 1972); J. March, "Advanced Organic Chemistry", 3rd ed., (John Wiley & Sons, New York, 1985); Fieser and Fieser, "Reagents for Organic Synthesis", Volumes 1-end (Wiley Interscience, New York). Likewise, the present invention has application in essentially any synthetic reaction which may be conducted in solution or on solid phase supports, including acetal formation, alkylations, alkynation, chiral alkylation, reductive alkylation, carbanion reactions, Grignard reactions, organiocadmium/aganese reactions, organolithim reactions, organozinc reaction, carbene insertion, condensations, Claisen reactions, aldol reactions, Dieckmann cyclization, Knoevenagel condensations, mannich reactions, cycloadditions, cyclizations (in particular to form heterocyclic rings), Friedel-Crafts reactions, halogenation, bromination, chlorination, nucleophilic addition, Michael addition, aromatic nucleophilic substitution, Finkelstein reaction, Mitsunobu reaction, palladium (0) catalyzed reactions, Stille coupling, Suzuki coupling, Heck reaction, carbamate/urea formation, oxidation of primary alcohol to aldehyde, Sharpless reaction, oxidation of secondary alcohol to ketone, oxidation of aldehyde to carboxylic acid, epoxidation, oxidation of primary chloride to aldehyde, oxidative phenol coupling, reduction of acid to alcohol, reduction of aldehyde to alcohol, reduction of alkyne to alkene, reduction of amide to amine, reduction of aryl nitro to amine, reduction of azide to amine, reduction of ester to alcohol, reduction of imine to amine, reduction of iodide to alkyl, reduction of ketone to alcohol, Witting reaction, Horner-Emmons condensation, and the like (see generally, "Solid Phase Organic Chemistry (SPOC)" and "Solid Phase Inorganic Chemistry (SPIC)", Chiron Mimotopes, pp. 1–31 (August 1995).

A "combinatorial library" is a collection of compounds in which the compounds comprising the collection are composed of one or more subunits or monomeric units (i.e. synthons). The subunits may be selected from natural or unnatural moieties including amino acids, nucleotides, sugars, lipids, carbohydrates, dienes, dienopholes, and the like. The compounds of the combinatorial library differ in one or more ways with respect to the type(s), number, order or modification of the subunits comprising the compounds.

Combinatorial libraries generated by the methods of the present invention may be screened for pharmacologically or diagnostically useful compounds, as well as for desired physical or chemical properties. It will be clear to one skilled in the art that such screening may be conducted on a library of compounds which have been separated from the polyvalent support, or may be conducted directly on the library of compounds which are still linked to the polyvalent support.

Figure 1:
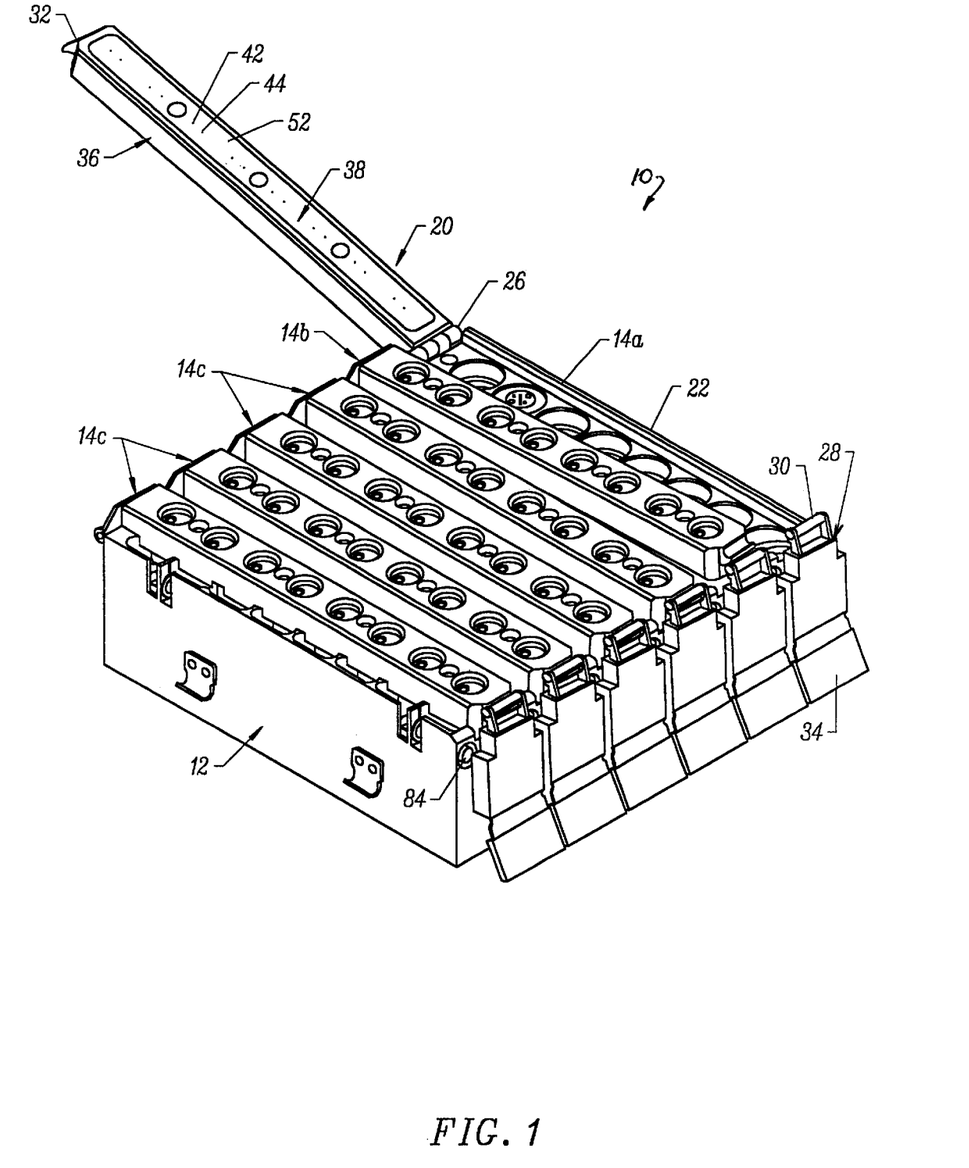
FIG. 1 is a perspective view of a synthesis apparatus having a plurality of cassettes according to the present invention.
Figure 4:
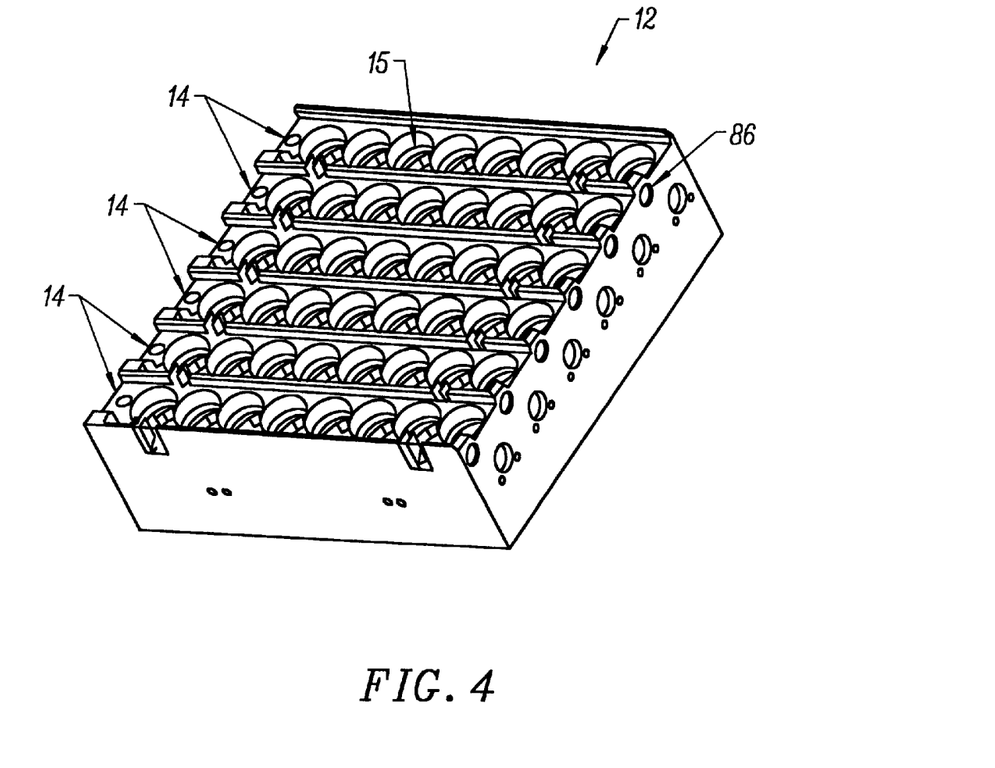
FIG. 4 is perspective view of a frame of the synthesis apparatus without the reaction vessels.

Referring now to FIGS. 1 and 4, a synthesis apparatus 10 according to the present invention will be described in detail.

Figure 2:
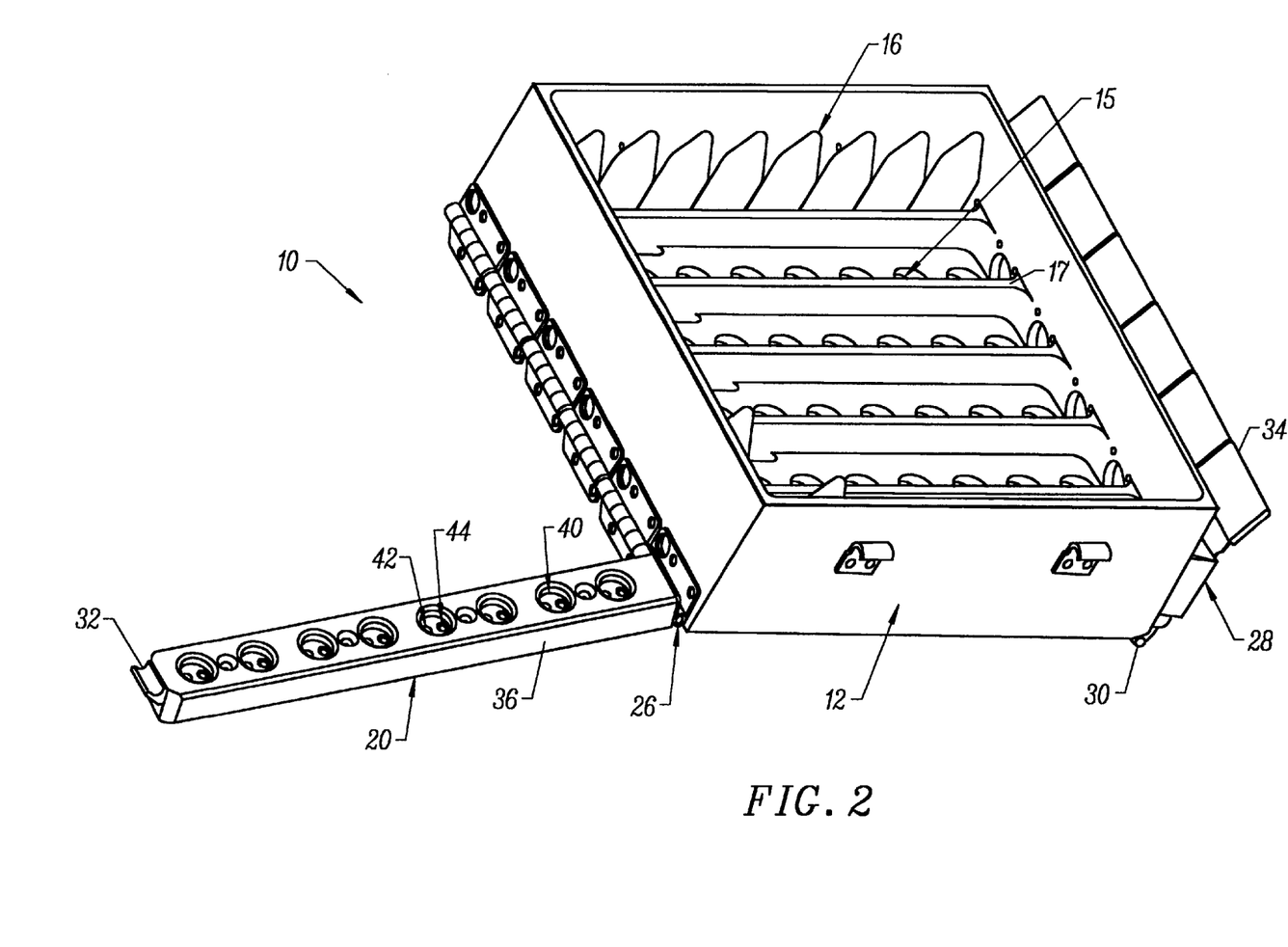
FIG. 2 is a perspective view of the bottom of the synthesis apparatus of FIG. 1.
Figure 18:
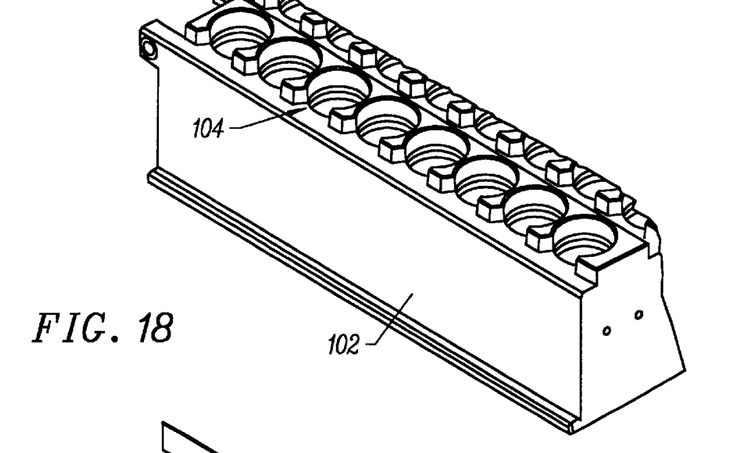
FIG. 18 is a partial view of the frame of the apparatus of FIG. 17.

As shown, synthesis apparatus 10 generally includes a frame 12 housing a plurality of elongate cassettes 14 disposed adjacent to each other, with each row or cassette 14 having a plurality of reaction vessel-holding openings 15 for mounting reaction vessels 16 (see FIGS. 2, 3, 11 and 12) to frame. The frame 12 preferably has a frame handle (not shown) made of epoxy resin which allows an operator to grip the frame. The resin material is substantially resistant to temperature changes encountered by the frame. In the preferred embodiment, cassettes 14 are formed as one integral unit having longitudinal ribs 17 separating adjoining cassettes 14 (see FIG. 2). Alternatively, cassettes 14 may be manufactured as individual parts that are coupled together, or they may remain separate from each other. In further embodiments, the cassettes 14 may be integrated into the frame 12 in a continuous body configuration for supporting reaction vessels 16 (FIG. 18). In exemplary embodiments, apparatus 10 will include six (6) cassettes, with each cassette 14 having eight (8) reaction vessels 16 to provide an array of forty-eight (48) reaction vessels. Of course, it will be recognized that the present invention is not limited to these numbers and any combination of the above can be used. For example, apparatus 10 may comprise eight (8) cassettes with six (6) reaction vessels within each cassette. Alternatively, apparatus 10 may have twelve (12) cassettes of eight (8) reaction vessels each to provide an array of ninety-six (96) reaction vessels 16, or any other desired combination.

In addition, it should be understood that the reaction vessels 16 do not have to be oriented linearly so as to form square array of vessels mounted within frame 12. For example, the reaction vessels 16 may be oriented in a circular fashion, with each cassette 14 having a concentric annular shape. Alternatively, the reaction vessels 16 may have other configurations, such as triangular, pentagonal or hexagonal fashion.

Synthesis apparatus 10 will include a heat exchanger (not shown), such as an electrical heater or hot water, hot air or steam, for heating the reaction vessels during certain reactions. Preferably, the heat exchanger comprises a fan for delivering hot air uniformly to the bottom of each reaction vessel. Similarly, cold air or gas may be delivered to the reaction vessels for reactions at below ambient temperature. The heat exchanger preferably flows heated or cooled air over the exposed portions of vessels 16 through the open underside of the frame 12.

Apparatus 10 may also include a mixing apparatus (not shown) for mixing the reaction media within vessels 16. In a preferred embodiment, the entire frame 12 is reciprocated by a suitable drive to mix the contents of vessels 16. A suitable agitation system is described in U.S. Provisional Patent Application Serial No. 60/063,134 entitled "Systems and Methods for Combinatorial Synthesis of Arrays of Reaction" filed on Oct. 22, 1997, previously incorporated herein by reference. Alternatively, the apparatus may include suitable agitators, such as a magnetic or ferrous plungers, stir bars, balls, beads, columns, disks or the like, which move within the reaction vessels 16 under an external force, e.g., a magnet.

Figure 3:
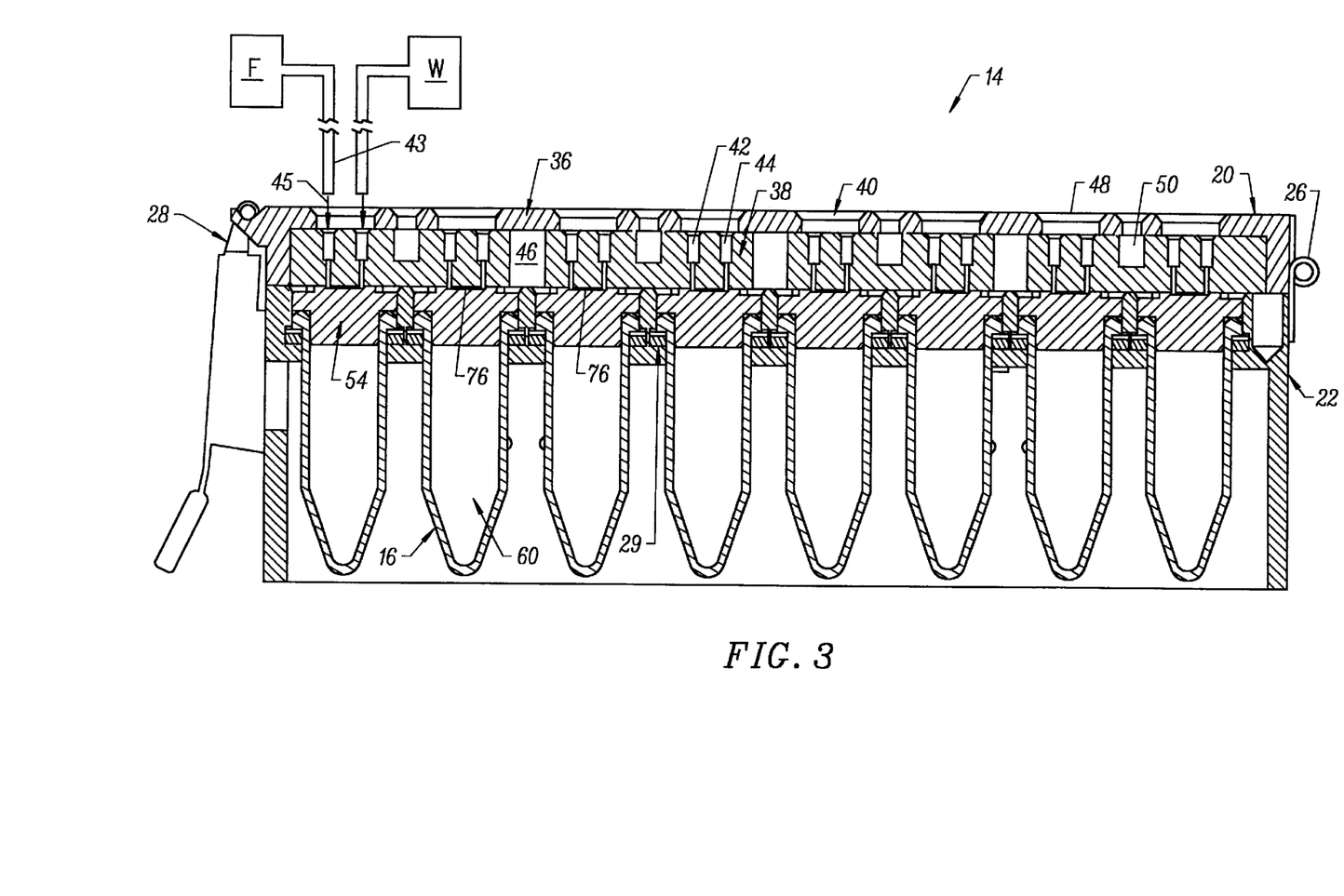
FIG. 3 is side cross-sectional view of one of the cassettes having a plurality of reaction vessels.

FIG. 3 illustrates a single cassette 14 in cross-section. As shown, each cassette 14 may be covered by a lid 20 pivotally coupled to a cassette body 22 by a hinge 26. In some embodiments, the hinge 26 is integrally formed with the lid 20 (FIG. 18). Lid 20 can be pivoted from the open position shown in FIG. 1 to the closed position shown in FIG. 3. A latch 28 is coupled to body 22 on the opposite side of hinge 26 for tightening lid 20 in the closed position to provide a gas-tight seal for reaction vessels 16. As shown in FIG. 1, latch 28 preferably includes a rod 30 that engages a metal lip 32 of lid 20, and a handle 34 for pulling rod 30 and lip 32 downwards to close lid 20 and seal reaction vessels 16.

As discussed below, each reaction vessel 16 is biased upward against lid 20 by a spring or bias element 29 positioned between each vessel 16 and cassette body 22. In the embodiment of FIG. 3, bias element 29 helps to ensure the integrity of the seal between a sealing surface of fluid manifold 38 and a sealing surface of a cap vent 54 during synthesis. Typically, the bias element 29 and lid 20 help to maintain about an 18–20 psi seal with the manifold 38. When pressures in the reaction vessels 16 exceed this level, the bias elements 29 in this embodiment act as pressure release mechanisms for each individual reaction vessel 16. This allows the venting of excess pressure from one reaction vessel 16 without interfering with the seal and synthesis reactions occurring in adjacent reaction vessels.

FIG. 1 illustrates one of the cassettes 14a with the lid 20 in the open position, one of the cassettes 14b with the lid 20 positioned over the reaction vessels 16 but not locked down by the latch 28, and the remainder of the cassettes 14c with the lid 20 closed and locked. It should be noted that apparatus 10 may include a single lid (not shown) that closes onto all of the cassettes 14. However, applicant has found that separate lids are preferable because they do not require as much force to close and lock. For example, a single lid would require sufficient force to overcome the resistance of 48 springs, rather than the 8 springs of a single cassette. In addition, having separate lids for each cassette 14 allows the operator to open a lid and access a reaction vessel without disturbing the other cassettes. Thus, if one of the vessels is leaking during simultaneous reactions, the operator may access that vessel without disturbing the reactions in the other seven cassettes. Of course, each reaction vessel 16 may also have its own separate lid. However, this would increase the cost of manufacturing and the amount of time required to operate the apparatus.

Figure 6:
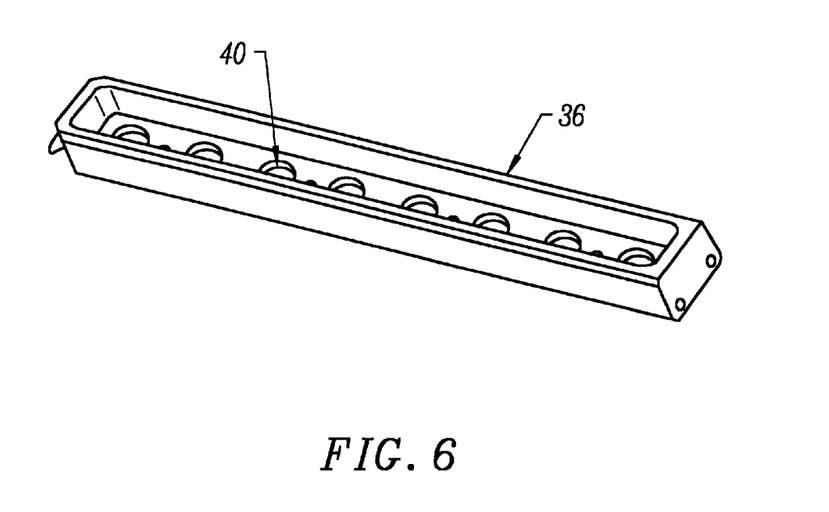
FIGS. 6 and 7 are bottom and top views, respectively, of a cassette stiffener for each of the cassettes.
Figure 7:
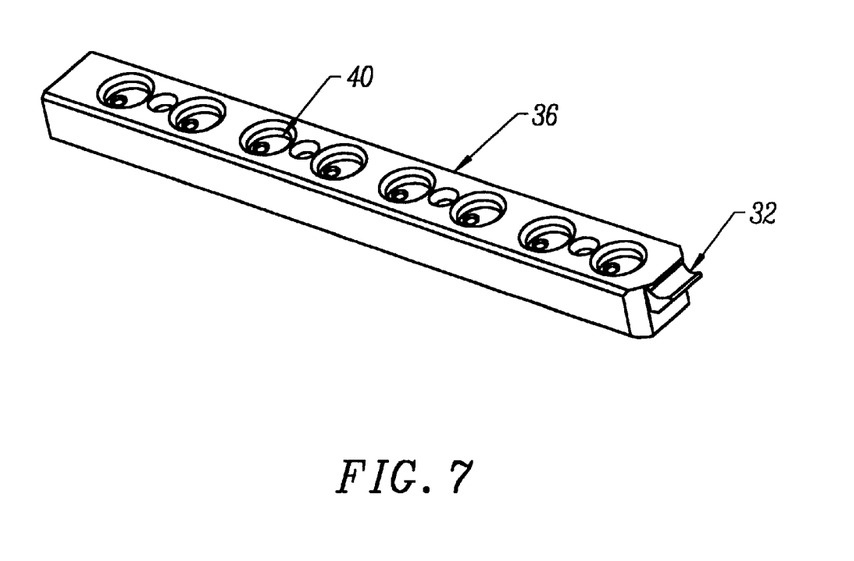

As shown in FIGS. 1 and 3, each lid 20 preferably includes a stiffener 36 (see also FIGS. 6 and 7) made of a strong load bearing material, such as aluminum. As the apparatus is preferably used to engage an interphase head containing a fluid conduit, the lid 20 may also include alignment protrusions or indentations to facilitate interphase alignment with the apparatus. A suitable interphase head is described in U.S. Provisional Patent Application Serial No. 60/063,134 entitled "Systems and Methods for Combinatorial Synthesis of Arrays of Reaction" filed on Oct. 22, 1997, previously incorporated herein by reference.

Figure 8:
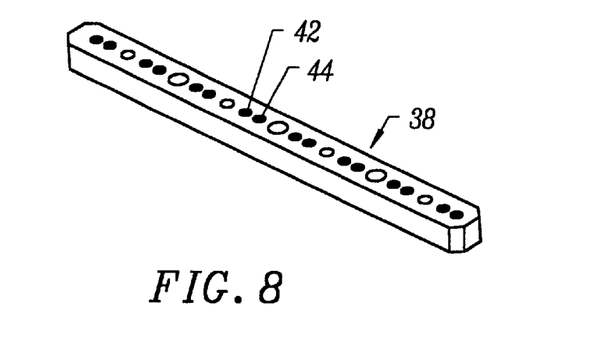
FIGS. 8–10 are top, bottom and side cross-sectional views, respectively, of a fluid manifold for each of the cassettes.
Figure 9:
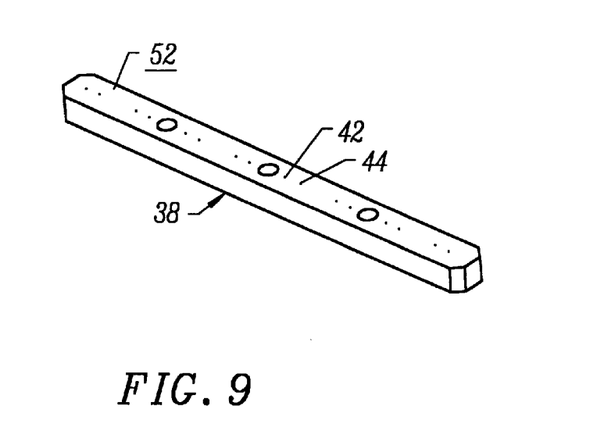
Figure 13:
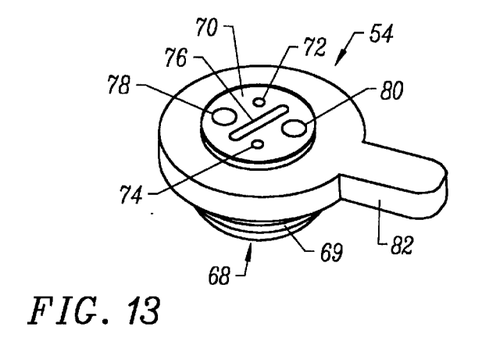
FIGS. 13 and 14 are top and bottom perspective views, respectively, of a cap valve for a reaction vessel.
Figure 17:
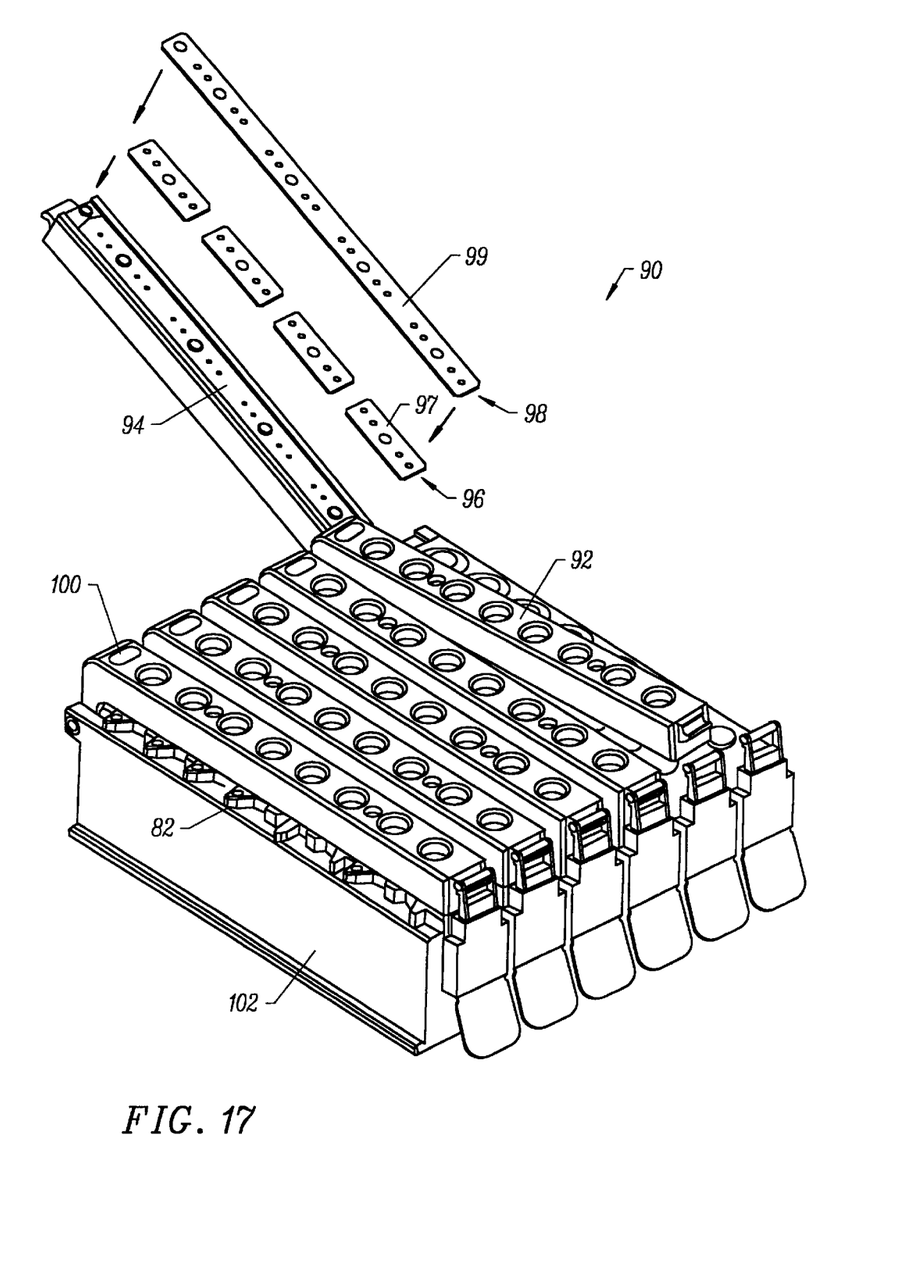
FIG. 17 is perspective view of a preferred embodiment of the synthesis apparatus.

The lid 20 typically contains a fluid manifold 38 (see also FIGS. 8–10) that is mounted within a recess of stiffener 36. The manifold may be attached to the lid 20 using a variety of press fit pins or other attachment methods. Manifold 38 will generally comprise a material that is inert and does not absorb chemicals from passing fluids such as brand polytetrafluoroethylene, glass, ceramics, synthetic plastics, e.g., Kel-F®, a polytrifluorocholoroethylene, metals, such as stainless steel or aluminum, or the like. Preferably, manifold 38 comprises a synthetic organic polymeric material, such as Teflon®. In some embodiments as shown in FIG. 17, the manifold 38 may include a layer 96 of elastomeric material such as Kalrez® a perfluoroelastomer to provide improved sealing characteristics with sealing surface or outer sealing surface 70 of cap vent 54 (FIG. 13). The layer 96 may be separate or integrated with the manifold. Preferably, the elastomeric layer 96 will be able to provide sufficient elasticity or resilience maintain a seal with the cap vent 54 over a temperature range from about −40° to 150° C. A protective layer of friction-resistant material such as FEP (fluorinated ethylene propylene) may be attached to layer 96 to reduce frictional damage that may result during the sliding or rotational motion of the cap vent 54.

Figure 10:
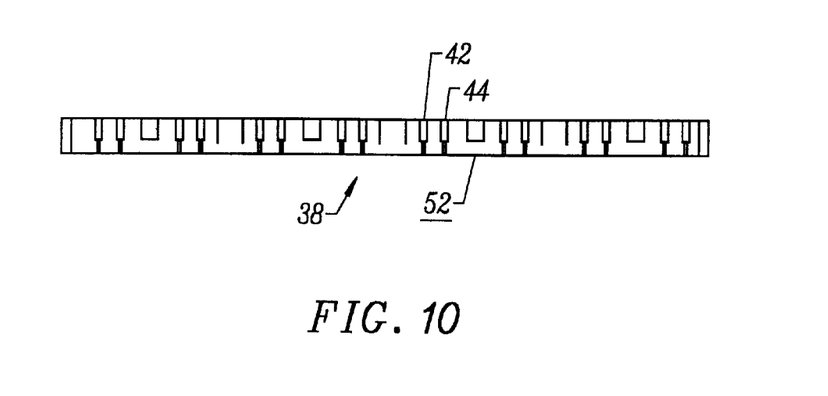

As shown in FIG. 3, stiffener 36 of lid 20 includes a plurality of holes 40 each positioned directly over a reaction vessel 16 when lid 20 is in the closed position. Similarly, manifold 38 includes first and second manifold passages 42, 44 extending through manifold 38 and aligned with each of the holes 40 of stiffener 36. Hole 40 and passages 42, 44 will be fluidly coupled to a fluid supply system including a fluid or reagent source F, a waste container W, and a fluid conduit 43 for supplying fluids, such as reagents and solvents, to reaction vessel 16. Fluid passage 42 generally functions as an inlet passage for delivering the reagents into the reaction vessel 16 to complete chemical reactions therein, while passage 44 functions as a gas vent to allow fluid flow into the reaction vessel 16; further description of this method is detailed below. Vent passage 44 may be plumbed to a number of waste containers (not shown), which are vented into an evacuated hood (not shown). The slight vacuum in the hood creates a slight vacuum in the vent line for withdrawing gases and toxic vapors from vessels 16. As shown in FIG. 10, passages 42, 44 preferably have a larger diameter at the upper or fluid supply side than the lower or reaction vessel 16 side of manifold 38. As illustrated, these passages 42 and 44 are preferably slidably connectable with a portion of a fluid conduit 43, as indicated by arrow 45. Advantageously, and unlike septum-type access devices, this provides a connection that will not lose seal integrity with repeated use.

Figure 11:
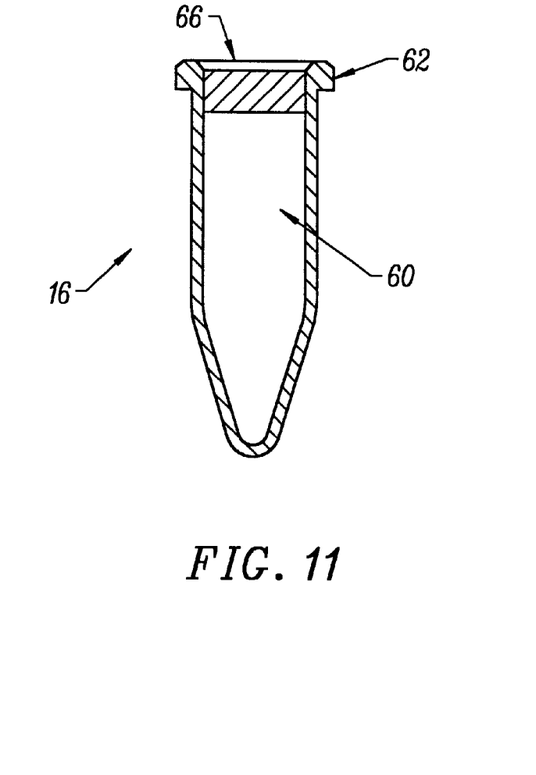
FIGS. 11 and 12 are side cross-sectional and perspective views, respectively, of a reaction vessel according to the present invention.
Figure 12:
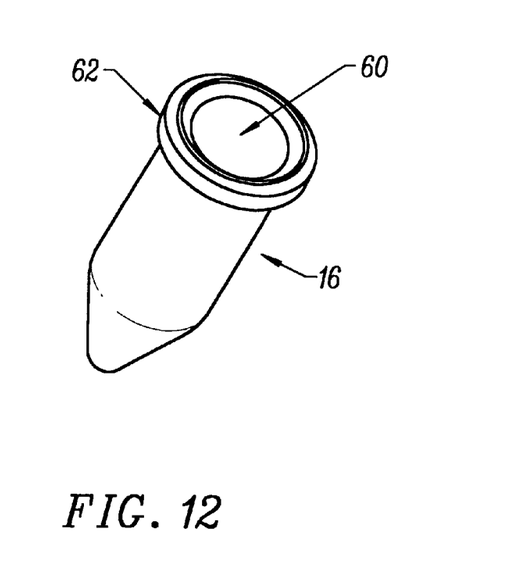
Figure 14:
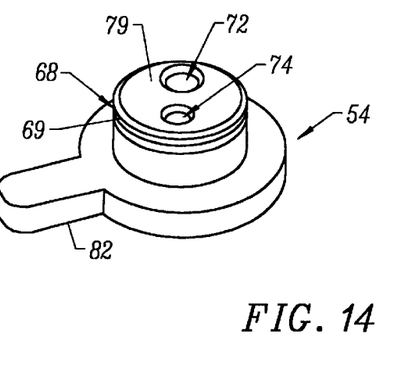

As shown in FIGS. 11 and 12, reaction vessels 16 can be conventional or specialized glass bottles defining an interior 60 for housing liquids or gasses and having an upper neck 62 for coupling reaction vessel 16 to a cap vent 54 (see FIGS. 13 and 14). The vessel 16 may have a rounded, pointed, or otherwise shaped bottom to facilitate distribution of fluid reagents to particles located in the lower portions of the vessel. In preferred embodiments, the bottom of the reaction vessel has a rounded configuration. Vessels 16 may further include a conduit (not shown) having an upper port extending above opening 66 and a lower port near the bottom of vessel 16 for allowing liquid to flow to and from interior 60 of vessel. A filter or frit 120 (FIG. 21), which preferably comprises a soft porous material such as Teflon®, plastic or stainless steel, may also be provided around the lower port of the conduit to inhibit solid impurities from entering the reaction vessel environment. In addition, vessels 16 may include a frit (not shown) at the lower portion of the vessels for supporting a synthesis support, such as a solid phase resin during draining operations. The frit will have a porosity appropriate to the type of solid support being employed and will comprise an inert material such as Teflon®, sintered glass, sintered metal, glass wool or ceramic.

Cap vent 54 (see FIGS. 13–15) preferably comprises an inert material which is machineable and dimensionally stable under reaction conditions such a Teflon® or a silica material. Preferably, the cap vent 54 or valve is located or aligned substantially over, typically vertically over, the reaction vessel 16 during synthesis operations. More preferably, the cap vent 54 is aligned with a longitudinal axis of the reaction vessel 16 as shown in FIG. 3. Cap vent 54 typically includes a hub 68 for insertion into opening 66 of vessel 16. Hub 68 preferably has a diameter slightly larger than opening 66 so that, when the cap vent 54 is pressed through opening 66 into interior 60 of vessel 16, the hub 68 generates a radial gas seal with opening 66 of the vessel 16. The inside diameter of vessel 16 is, in one embodiment, preferably about 0.004–0.008 inches smaller than an outside diameter of cap vent 54. This press fit coupling of cap vent 54 with the reaction vessel 16 ensures a good seal with the reaction vessel 16. Using a cap vent 54 of the present embodiment reduces the number of moving parts, as described further below. Alternatively, the hub 68 of cap vent 54 may also include outer threads 69 for threading coupling cap vent 54 to complementary threads (not shown) on the inside of vessel 16.

To control fluid entry into the reaction vessels 16, the fluid manifold 38 and cap vent 54 may be viewed as forming a first valve portion and a second valve portion respectively. As shown in FIGS. 13–16, cap vent 54 includes a rotatable valve surface 70. An inner surface 79 on hub 68 is shown in FIG. 14. Rotatable valve surface 70 (FIG. 13) may be considered a sealing surface for the second valve portion and is substantially planar to form a gas-tight seal with planar, sealing lower surface 52 of manifold 38. Surface 52 may be considered a sealing surface for the first valve portion (i.e. manifold 38). In alternative embodiments shown in FIG. 17, the sealing surface 97 of sheet 96 (which may be integrated with manifold 38), forms the seal with surface 70. Or surface 99 of protective sheet 98 forms the seal with surface 70. The sealing surfaces are slidably movable relative to one another. This slidable, preferably rotatable, movement allows the user to open or close access to the reaction vessel interior.

Figure 15:
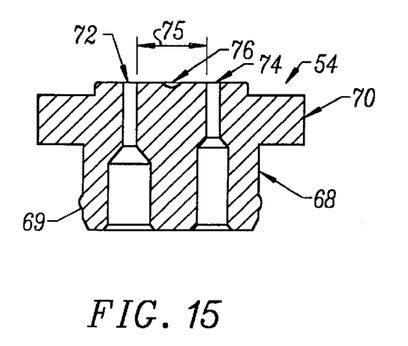
FIG. 15 is a side cross-sectional view of the cap valve illustrating liquid and vent ports.
Figure 16:
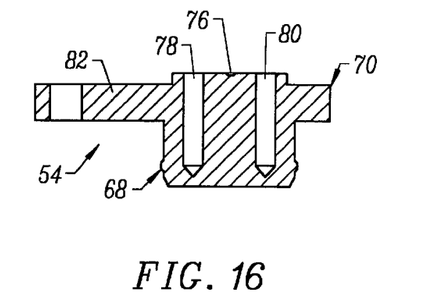
FIG. 16 is a side cross-sectional view of the cap valve illustrating holes for reducing the surface area of the cap valve.

Although not restricted in this manner, the first valve portion such as manifold 38 is typically located in the lid 20, while the second valve portion 54 is couplable to the reaction vessel 16. This embodiment (FIG. 3) creates a valve wherein the sealing surfaces are accessible and openable. When lid 20 is open, sealing surfaces on the fluid manifold 38 and cap vent 54 are separated. By dividing the valve into two portions, this allows part of the valve to be a disposable, consumable product. By creating the seal between parts such as on the fluid manifold 38 and cap vent 54 of the reaction vessel 16, the present invention advantageously allows greater flexibility in designing one part to be consumable and simpler to manufacture. Additionally, where the reaction vessel 16 rotates with the cap vent 54, the number of moving parts are reduced since the cap vent 54 has the dual role of being a plug for reaction vessel 16 while also being a rotatable surface 70 of the valve portion. Preferably, the cap vent 54 including hub 68 comprises a single, continuous part as shown in FIGS. 15 and 16. This continuous body configuration facilitates manufacturing and simplifies the design of the potentially disposable portions of the present apparatus. In some embodiments, the valve or sealing device used in the present invention may be viewed as having a nonrotatable part (manifold 38) and a rotatable part (cap vent 54 and reaction vessel 16).

As shown in FIG. 15, first and second fluid passages 72, 74 extend through cap vent 54 to the interior 60 of reaction vessel 16. In the preferred configuration, passage 72 functions as an inlet passage while passage 74 functions as a vent passage to allow venting of gasses while liquid is being delivered into the reaction vessel 16. Passages 72, 74 preferably have a larger diameter at the lower or vessel side of cap vent 54 than at the upper or sealing surface 70 side of the cap vent. The passages are typically separated by a bypass distance indicated by arrow 75.

As shown in FIGS. 13 and 15, cap vent 54 further includes a bypass path such as a linear groove 76 formed in sealing surface 70 between fluid passages 72 and 74. Groove or bypass path 76 functions to allow washing of the fluid distribution passages 42, 44 in manifold 38, as discussed in further detail below. When the bypass path is linear groove 76, the groove 76 preferably has a length substantially equivalent to the bypass distance and the diameters of the passages 72 and 74. Preferably, a U-shaped passage is formed with passages 42 and 44 when the cap vent 54 is positioned in the closed and flushing position of FIG. 3. This provides a "zero dead volume" system where reagents or solvents introduced into the system are either in the sealable portions of the reaction vessel 16 or they are in passages such as 42 and 44 which can be completely flushed to remove contaminants before the next reagent or solvent wash. Zero dead volume may be defined as having a fluid delivery path leading right to the entrance of the reaction vessel 16 (i.e. opening of passages 72, 74) that can be completely flushed to remove contaminants, preferably while reactions are still occurring in the reaction vessel and without disturbing the reaction therein. In a further embodiment, sealing surface 70 further includes a pair of holes 78, 80 that extend through a portion of (but not completely through) cap vent 54 (FIGS. 13 and 16). Holes 78, 80, which are optional, function to decrease the total surface area of sealing surface 70 that must be sealed with lower surface 52 of manifold 38. This is because manifold 38 does not have to provide a seal over holes 78, 80. In addition, it should be noted that the escape path of liquid from passages, 72, 74 is shorter to the edge of sealing surface 70 than it is to holes 78, 80. Therefore, the addition of these holes 78, 80 does not increase the likelihood of gas or fluid leakage from passages 72, 74.

Figure 5:
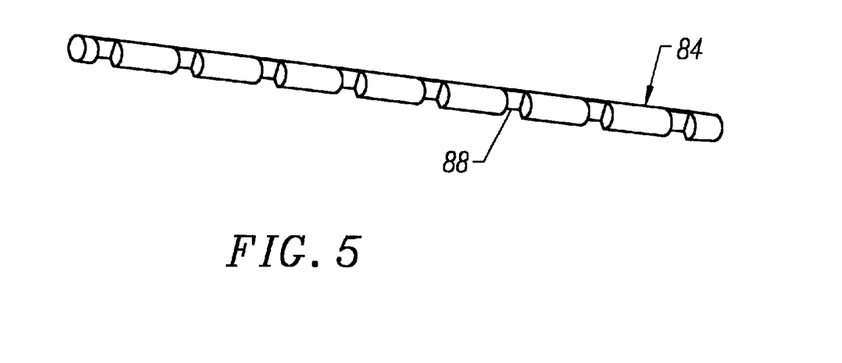
FIG. 5 is a perspective view of an actuator rod for opening and closing cap valves on each of the reaction vessels.

Cap vent 54 further includes a handle or radial extensor 82 that engages an actuator rod 84 (see FIGS. 1 and 5) for rotating each of the cap vents 54 within cassettes 14 between open and closed positions. Actuator rods 84 each extend within a longitudinal groove 86 (see FIG. 4) in each cassette 14. Actuator rods 84 include a plurality of grooves 88 longitudinally spaced for receiving handles 82 of each of the cap vents 54. Actuator rods 84 are each coupled to a suitable drive motor (not shown) for linear movement of rods 84 relative to each cassette 14. This linear movement causes handles 82 to move with rod 84, thereby rotating cap vents 54 and reaction vessels 16 relative to manifold 38. In essence, the cap vents are acting as valves. In the open position, passages 72 and 74 of cap vent 54 are aligned with passages 42 and 44 of manifold 38 so that liquid can pass through passage 42 and passage 72 into the interior of the vessel 16, while gas is vented through passage 74 and passage 44. In the closed position shown in FIG. 3, cap vent 54 is rotated such that passages 42 and 42 of the manifold are aligned with groove 76. As shown in FIG. 3, this completes a fluid path between passages 42 and 44 so that the passages can be washed with a fluid, such as a solvent, to remove any remaining liquid or other fluid that may be left on the inside walls of this passages. The passages 42, 44 and 72, 74 are misaligned in the closed position to close access to the reaction vessel 16.

In operation, each of the cassettes 14 are closed and locked by closing lids 20 and locking latches 28 (see FIG. 1). A drive motor is then actuated to drive actuator rod 84 and thereby rotate cap vents 54 into the open position (not shown). Fluid, such as a reagent, is then delivered sequentially or simultaneously from a suitable reagent source through the fluid delivery system into holes 40 of lids 20. The fluid passes through inlet passages 42 and 72, and through the vessel conduits to the interior of reaction vessels 16. As the fluid enters reaction vessels 16, the air or gas within the vessels is vented through passages 74 and 44.

When the vessels have been filled with the selected volume of reagent, actuator rods 84 are driven linearly to rotate cap vents 54 into the closed position (see FIG. 3). The simultaneously opening and closing of cap vents 54 in each cassette 14 allows for the parallel distribution of fluids to the reaction vessels, which increases the speed of the entire procedure.

In the closed position, passages 42, 44 are aligned with groove 76 to form a closed loop that is isolated from the interior of the reaction vessel 16. Therefore, during the reactions, the fluid supply system and passages 42, 44 may be purged with a solvent by delivering the solvent through one of the passages 42, groove 76 and the other passage 44. This saves considerable time and allows the entire fluid distribution system to be washed while the reactions are occurring in reaction vessels 16. In addition, groove 76 allows purging of the fluid delivery system after, for example, cassette 14 has been removed from the rest of the fluid delivery system. This allows the fluid delivery system to be purged of gases, vapors, oxygen or other contaminants, while the valve maintains a closed inert environment.

In a further embodiment of the present invention shown in FIGS. 17–20, the synthesis apparatus 90 incorporates a lid 92 with a manifold 94 having elastomeric layers 96. The layers 96 may be further covered with a protective layer 98 of material such as FEP. It should be understood that these layers 96 and 98 may be integrally formed or incorporated with the manifold 94. The elastomeric layer 96 provides sufficient resilience to maintain a seal with the cap vent 54 over a temperature range from about −40° to 150° C. The lid 92 includes an alignment hole 100 to provide a "go, no-go" feature to the synthesis apparatus 90. An interphase head (not shown) will have protrusions which mate with the alignment hole 100. When the protrusions are misaligned with holes 100, the "go, no-go" quality of holes 100 prevent engagement with the interphase head during incorrect alignment. The protrusions on the head prevent the head from being lowered in a misaligned position which may damage the apparatus 90 or the interphase head.

Referring to FIG. 18, the frame 102 used with apparatus 90 is a continuous body with reaction vessel holders or cassettes 14 integrated with the frame as shown in FIG. 18. This facilitates manufacturing of the frame 102. The frame 102 has a substantially horizontal opening 104 for each reaction vessel 16. The handle or radial extensor 82 of cap vent 54 protrudes from this opening 104 and allows the cap vent to be opened or closed during operation of apparatus 90.

Figures 19, 20:
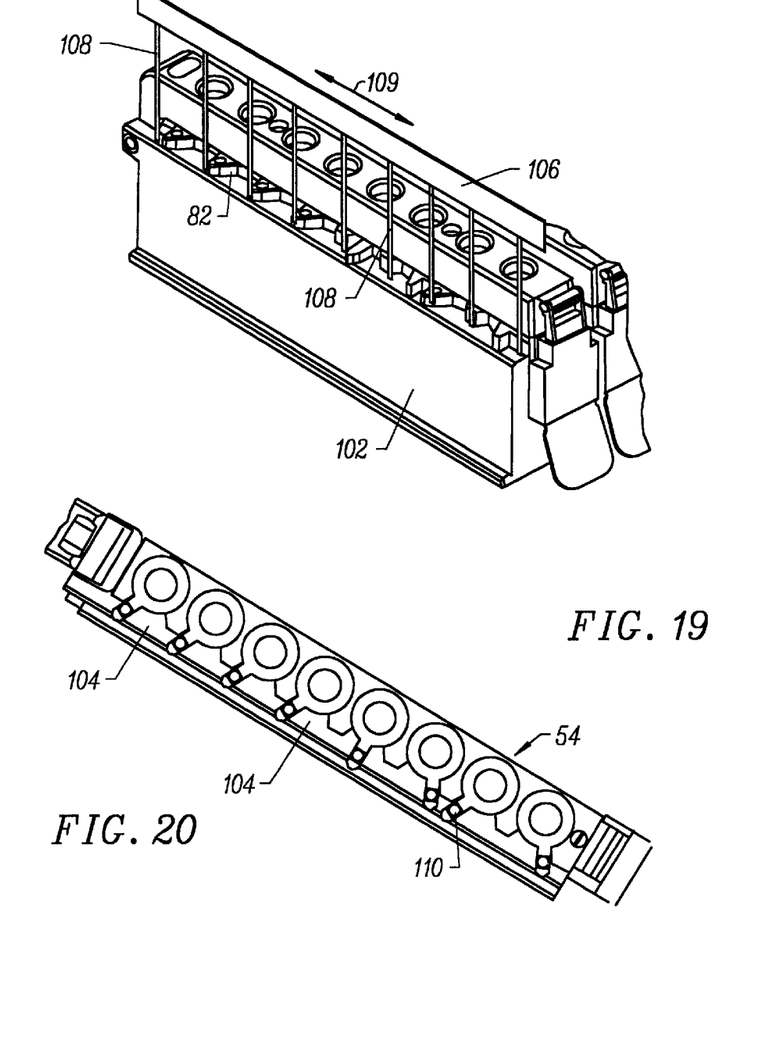
FIG. 19 shows a rack used to actuate cap vents in the apparatus of FIG. 17.
FIG. 20 is an overhead view of the cap vents in the frame of the apparatus shown in FIG. 17.

Referring to FIG. 19, the cap vents 54 are preferably actuated by a rake 106 which has a plurality of engagement elements such as pins 108. In FIG. 19, nine (9) pins 108 are used with eight (8) cap vents 54 to provide simultaneous actuation of the caps. Nine pins 108 are used so that the cap vents 54 can be opened or closed irregardless of the position (open or closed) which the cap vent is in. In one embodiment, the pins 108 are spaced to engage the sides of handle 82 to open or close the vents. The pins 108 will land at points along the frame 102 where the handles 82 are not located. Then movement, as indicated by arrow 109, will cause the rake 106 to engage the handles 82. In further embodiments, the pin 108 engages a hole 110 or recess in the handle or other portion of the cap vent. In some embodiments, the pins 108 may be individually retractable from the hole so to allow individual valves to be opened or closed without interfering with the positions of the other valves (FIG. 20). The range of motion of each handle 82 typically is limited by the size of opening 104 as shown in FIG. 20.

Figure 21:
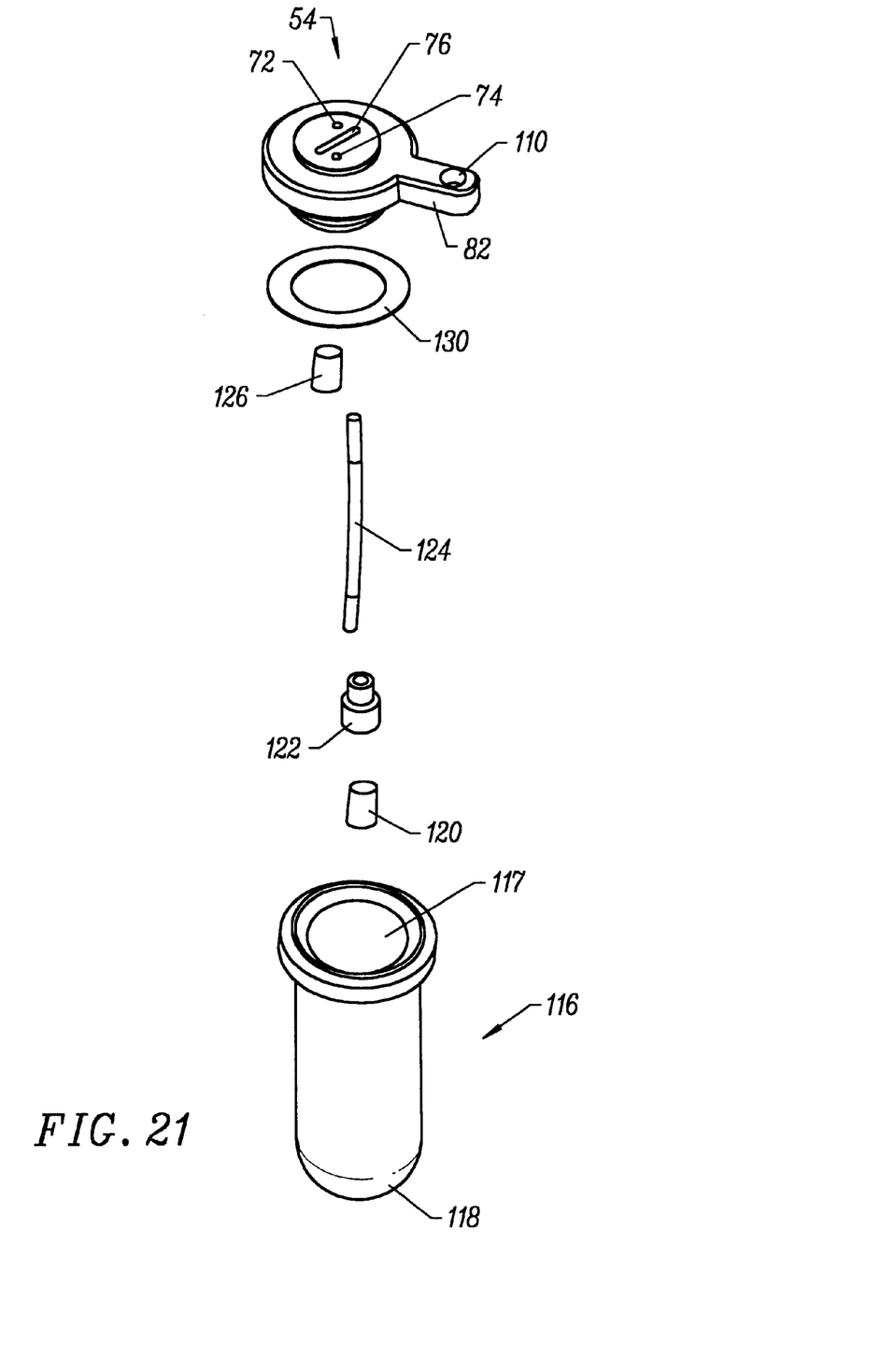
FIG. 21 is an exploded view of a further embodiment of a reaction vessel according to the present invention.

Referring now to FIG. 21, a further embodiment of the reaction vessel 116 will be described. The vessel 116 is characterized by an open top 117 and a rounded lower surface 118. This surface 118 improves the circulation of reagents among materials located at the bottom of the reaction vessel. In this exemplary embodiment, the cap vent 54 is shown with groove 76 and passageways 72 and 74. The cap vent 54 does not have openings 78, 80 to reduce the chances that these opening might damage elastomeric surfaces on sheet 96. This embodiment of reaction vessel 116 also has a reduced frit 120 which is mounted in a holder 122. As the frit 120 can now be molded into a simpler shape, this facilitates the manufacturing of smaller frits. The frit holder 122 is coupled to tube 124, preferably made of inert material, which is attached to the cap vent 54 at passage 74. The other frit 126 may be coupled to passage 72. For reaction vessel 116, an annular ring 130 of elastomeric material such as Kalrez® maintains a seal between the cap vent 54 and the reaction vessel 116 over the wide range of temperatures such as between about −40° to 150° C. that may be encountered during synthesis. Alternatively, the ring 130 may be coated with an inert material to prevent corrosion to the elastomeric material.

While the above is a full description of the specific embodiments, various modifications, alternative constructions and equivalents may be used. For example, the holes 78 and 80 may have rounded, tapered upper edges to reduce frictional damage to the fluid manifold or sheet 96 during valve rotation. The bypass path 76 is not restricted to being located on an upper surface of the cap vent. The path may be a curved passage that is defined within the cap vent. The bypass path may also extend through and/or below the cap vent via tubing or other devices. Further, the cap vent may be a translational-type valve which uses linear translation rather than rotational motion to open and close access to the reaction vessels. It should be understood that the present invention may have both the first and second valve portions located in the lid while a plug having first and second passages 72, 74 is mounted with the reaction vessel 16. In some embodiments, one valve portion is movable while the other portion is not. Alternatively, the movable valve portion may translate, instead of rotating relative to the other valve portion. The manifold may be a one-piece or multiple-piece manifold. The bias element may comprise of a variety of devices such as a elastomeric layer or a coil spring. The cap vent may also have additional positions besides the first and second positions described. For example, a third position may have the valve closed, but does not engage the bypass path with passages in the manifold. Or the third position may direct fluid into additional passages in the cap vent or the manifold. Additionally, the movable valve portion may located or aligned above the lower movable valve portion, or vice versa. Other orientations of the valve portions such as horizontal or angular may also be used.

What we claim is:

1. A synthesis apparatus comprising:
   a frame having a plurality of reaction vessel-holding openings for holding a plurality of reaction vessels;
   a plurality of valves;
   said reaction vessel-holding openings and said valves aligned with one another;
   each said valve being movable between an open position, allowing fluid to be delivered through the valve, and a closed position, preventing fluid from passing through the valve; and
   wherein each of said valves comprises:

a first valve portion having a first sealing surface;
a second valve portion having a second sealing surface;
wherein the first surface and the second surface are slidably movable relative to one another;
said second valve portion comprising a separate cap vent movable between first and second positions corresponding to the open and closed positions of said valve, wherein said cap vent provides access to an interior of one said reaction vessel;
said first valve portion defining a first manifold passage and a second manifold passage; and
each said cap vent defining a bypass path, said bypass path connecting the first manifold passage to the second manifold passage when said cap vent is in the second position.

2. A container for use with a combinatorial synthesis apparatus of the type comprising a first valve portion defining first and second fluid passages, said container comprising:
a reaction vessel having an interior and an open top;
a second valve portion mountable to said open top of the reaction vessel;
the second valve portion comprising an outer sealing surface, sealingly engageable with the first valve portion, and an inner surface facing the interior;
the second valve portion defining first and second fluid passages extending between the outer and inner surfaces; and
said second valve portion defining a fluid path extending between first and second positions on the outer sealing surface, said first and second positions alignable with the first and second fluid passages of the first valve portion when the second valve portion is in a closed position, whereby said first and second fluid passages of the first valve portion and the fluid path define a generally U-shaped bypass passage.

3. A container as in claim 2 wherein said first and second fluid passages of said second valve portion open on to said outer surface at third and fourth positions, said third and fourth positions separated by a distance equal to the distance between the first and second positions.

4. A container as in claim 2 wherein said fluid path comprises a groove on said outer surface of said second valve portion.

5. A container as in claim 2 wherein said second valve portion is rotatable relative to the first valve portion.

6. A container as in claim 2 wherein said second valve portion has a radial extensor for rotating the second valve portion.

7. A method for accessing an interior of a reaction vessel for use in combinatorial synthesis, the method comprising:
accessing a frame comprising a plurality of reaction vessels aligned with a plurality of valves, each said valve comprising first and second valve portions;
slidably engaging a fluid conduit to a first passage in each said first valve portion, said fluid conduit coupled to a fluid source, said first valve portion defining a second passage;
simultaneously actuating said plurality of valves by simultaneously rotating said second valve portions by moving a rake directly coupled to each said second valve portion, thereby moving each said second valve portion to align first and second passages in said second valve portion with said first and second passages of a corresponding said first valve portion to provide access to the interior of a corresponding said reaction vessel; and
flowing fluid from the fluid conduit into said interiors of the reaction vessels through said first passages while simultaneously venting said interiors of the reaction vessels through the second passages.

8. A method for accessing an interior of a reaction vessel for use in combinatorial synthesis, the method comprising:
accessing a frame comprising a plurality of reaction vessels aligned with a plurality of valves, each said valve comprising first and second valve portions;
slidably engaging a fluid conduit to a first passage in each said first valve portion, said fluid conduit coupled to a fluid source, said first valve portion defining a second passage;
simultaneously rotating each said second valve portion to align a bypass path with the first and second passages in each said first valve portion by moving a rake directly coupled to each said second valve portion;
flowing fluid from each said first passage of said first valve portion through a corresponding said bypass path to a corresponding said second passage of said first valve portion;
simultaneously rotating each said second valve portion to align a first passage in said second valve portion with said first passage of a corresponding said first valve portion to provide access to the interior of a corresponding said reaction vessel; and
flowing fluid from the fluid conduit, through the first passages and into said interiors of the reaction vessels.

9. A method for accessing an interior of a reaction vessel for use in combinatorial synthesis, the method comprising:
accessing a frame comprising a plurality of reaction vessels aligned with a plurality of valves, each said valve comprising first and second valve portions;
slidably engaging first and second fluid conduits to first and second passages in each said first valve portion, said first fluid conduit coupled to a fluid source;
simultaneously rotating said second valve portions by moving a rake directly coupled to each said second valve portion, thereby moving each said second valve portion to align a first passage in said second valve portion with said first passage of a corresponding said first valve portion to provide access to the interior of a corresponding said reaction vessel;
simultaneously rotating each said second valve portion to align a bypass path formed in the second valve portion with the first and second passages of the first valve portion to define a U-shaped bypass passage; and
flowing fluid from the first fluid conduits, through the U-shaped bypass passages, and into said second fluid conduits.

* * * * *